United States Patent [19]

Roos et al.

[11] Patent Number: 4,623,620

[45] Date of Patent: Nov. 18, 1986

[54] ENUCLEATED GRANULOCYTES, THEIR PREPARATION AND USE

[75] Inventors: Dirk Roos, Amsterdam; Alwin A. Voetman, Badhoevedorp; Louis J. Meerhof, Hoogwoud, all of Netherlands; Bertram Lubin, Oakland, Calif.

[73] Assignee: Stichting Vrienden Van De Stichting Dr. Karl Landsteiner, Amsterdam, Netherlands

[21] Appl. No.: 519,563

[22] Filed: Aug. 2, 1983

[51] Int. Cl.$^4$ .............................................. G01N 33/53
[52] U.S. Cl. ........................................ 435/7; 435/34; 435/29; 435/810; 435/4; 436/518
[58] Field of Search ................... 435/4, 7, 34, 29, 810; 436/519, 821, 63, 70, 512, 547, 518

[56] References Cited

U.S. PATENT DOCUMENTS

| | | | |
|---|---|---|---|
| 4,111,199 | 9/1978 | Djerassi | 436/63 |
| 4,235,869 | 11/1980 | Schwarzberg | 436/512 |
| 4,251,995 | 2/1981 | Pert et al. | 62/64 |
| 4,327,799 | 5/1982 | Scheiwe et al. | 62/62 |
| 4,328,183 | 5/1982 | Rosenfield et al. | 436/522 |

FOREIGN PATENT DOCUMENTS 2013211  1/1979  United Kingdom .

OTHER PUBLICATIONS

Voetman, A. A. et al., "Cryopreservation of Enucleated Human Neutrophilo (PMN Cytoplasts), Blood 63(1) 234-37 (1984).

Roos, D. et al., "Functional Activity of Enucleated Polymorphonuclear Leukocytes", J. Cell. Biology 97(2) 368-77 (1983).

Spendlove, R. S., "Optimal Labeling of Antibody with Fluorescein Isolhicyanate", Proc. Soc. Exptl. Biol. and Med. 122, p. 580 (1966).

Knight, et al., "Injury to Human Granulocytes at Low Temperatures" Cryobiology 17, 273-281 (1980).

Wigler et al., Biochem. Biophys. Res. Comm., vol. 63, No. 3, (1975) pp. 669-674.

Simanton et al., Proc. Natl. Acad. Sci. (USA), vol. 77, No. 8, Aug., (1980), pp. 4798-4802.

Shannon et al., Tissue Culture (Ed. Kruse et al.) Academic Press, 1973, pp. 712-718.

*Primary Examiner*—Christine M. Nucker
*Assistant Examiner*—Stephen C. Wieder
*Attorney, Agent, or Firm*—Brumbaugh, Graves, Donohue & Raymond

[57] ABSTRACT

Granulocytes, particularly neutrophilic granulocytes, also called polymorphonuclear leukocytes (PMN), have been found to retain their immunological properties after enucleation. Moreover, in contrast with normal granulocytes, enucleated granulocytes are stable when stored in frozen condition. The invention relates to the enucleated granulocytes, especially in frozen condition, to a process for preparing the enucleated granulocytes, to a process for assaying antibodies against granulocytes, and to a kit for carrying out the latter process.

12 Claims, No Drawings

ENUCLEATED GRANULOCYTES, THEIR PREPARATION AND USE

Human blood contains various cell types: erythrocytes (red cells), leukocytes (white cells) and thrombocytes (blood platelets). One of the functions of the leukocytes is the defense against infecting microorganisms. Leukocytes occur in the form of granulocytes, monocytes and lymphocytes. Each of these cell types has a specific function in the defense system of the blood. There exist three forms of granulocytes, namely neutrophilic, basophilic and eosinophilic granulocytes. Neutrophilic granulocytes, also called polymorphonuclear leukocytes (PMN), are active mainly in the defense against bacteria and fungi. Although the invention relates to enucleated granulocytes in general, their preparation and their use, the invention will be described and illustrated mainly with respect to neutrophilic granulocytes (polymorphonuclear leukocytes or PMN).

There are various reasons why patients may suffer from a lowered leukocyte content in their blood. One of these reasons is that, in the patient's blood, antibodies are formed against their own leukocytes. If this is the case, the leukocytes are destroyed, which results in serious, often life-threatening infections in the patient. A low leukocyte content may also be the result of disorders other than the production of antibodies. Therefore, it is highly desirable to establish the reason for a low leukocyte count as, otherwise, a proper therapy cannot be selected.

Generally, the detection of antibodies against blood cells presents no problem. The serum of the patient is incubated with blood cells of a normal donor. Any antibodies in the patient's serum will react with the donor cells, and the reaction may be detected by means of known optical or immunological methods. In practice, the patient's serum is tested with the blood cells of a number of different normal donors, as the antibodies may be directed to specific structures not generally present on the cells of any donor. This requires the availability, in the laboratory, of a series of typed donor blood cells. This is no problem with all types of blood cells other than granulocytes, as the cells may be stored in frozen condition. Granulocytes, and among these, neutrophilic granulocytes (PMN), differ from all other blood cells in that they are unstable in frozen condition. This means that an assay of antibodies against granulocytes in a patient's blood sample can be carried out only by drawing blood from a series of normal donors, isolating the granulocytes from the blood samples, and incubating these granulocytes with the patient's serum. This is a very tedious procedure which has seriously limited the assay of antibodies against granulocytes.

It has been found that the nucleus of granulocytes can be removed and that the enucleated granulocytes so formed retain the immunological properties of the intact granulocytes. An even more important finding was that the enucleated granulocytes may be stored in frozen condition without substantial deterioration. This allows storage of typed enucleated donor granulocytes which may be used in the assay of antibodies against granulocytes in a patient's serum sample.

Consequently, the invention relates in the first place to the new enucleated granulocytes, especially to enucleated polymorphonuclear leukocytes, in particular to these new cells in frozen condition.

Further, the invention relates to a process for preparing the enucleated granulocytes, which comprises ultracentrifuging a suspension of granulocytes over a discontinuous density gradient in the presence of a compound capable of inducing nuclear extrusion at a temperature of at least 25° C., and recovering the enucleated cells.

This process for preparing the enucleated cells is a modification of a process disclosed by M. H. Wigler and I. B. Weinstein in Biochem. Biophys. Res. Commun. 63 (3) (1975), pages 669–674. These authors used ultracentrifugation of mouse L cells over a discontinuous density gradient of Ficoll solutions (Ficoll is a synthetic high molecular weight polysaccharide) in the presence of cytochalasin B. The cells were split in enucleated and nucleated cells (cytoplasts and karyoplasts, respectively) which could be separated from each other due to their different densities.

According to the present invention it was found that this principle may be used for the preparation of enucleated granulocytes. Preferably, the density gradient consists of at least two aqueous solutions having densities in the range of 1.04 to 1.09 gram/cm$^3$ at 20° C., the density difference between two neighbouring layers being in the range of 0.005 to 0.020 gram/cm$^3$ at 20° C.

As a compound capable of inducing nuclear extrusion in cells a cytochalasin compound may be used. Several of such compounds have been described. The cytochalasin compound which is preferred in the process of the present invention is cytochalasin B.

The aqueous solutions used in the discontinuous density gradient should be substantially iso-osmotic with the cells. High molecular weight polysaccharide solutions are preferred. Good results have been obtained with aqueous Ficoll solutions. Ficoll is a high molecular weight polysaccharide sold by Pharmacia AB, Uppsala, Sweden.

Most preferably, the discontinous density gradient used in the present process comprises aqueous Ficoll 70 solutions having densities at 20° C. of 1.0855, 1.0578 and 1.0477 g/cm$^3$, each containing 20 $\mu$M of cytochalasin B, the layer of lowest density containing, before centrifugation, the cells to be enucleated, and the centrifugation is effected at about 81,000 g for about 10 to 30 minutes at 25°–40° C.

Under the above-mentioned preferred conditions the enucleated cells will concentrate at the interface of the upper and middle layers of the density gradient, and the nucleated cells will be pelleted on the bottom of the centrifugation tube.

Enucleation of polymorphonuclear leukocytes by centrifugation over a Ficoll gradient is a process that probably involves accumulation of the intact cells at the interface between the middle and lower Ficoll solutions (band 2), movement of nuclei and granules to the centrifugal side of the cells, fusion of the plasma membrane around the cytoplasmic (centripetal) and around the karyoplastic (centrifugal) parts of the cells, flotation of the cytoplasts to the interface between the upper and middle Ficoll solutions (band 1) and sedimentation of the karyoplasts to the bottom of the tubes (band 3). This order of events is deduced from the observations that centrifugation at a force of less than 81,000 x g resulted in localization of intact cells in band 2, whereas centrifugation at 81,000 x g resulted in practically complete division of the cells into separated cytoplasts and karyoplasts. The conclusion that a PMN cytoplast is "pinched off" from the rest of the cell is based on the low activity of lactate dehydrogenase in the gradient material after the formation of cytoplasts, on the structural integrity of the cytoplasts and on the "outside-out" configuration of the cytoplasts. The presence of a cytochalasin, such as cytochalasin B is essential for PMN cytoplast formation; apparently, the microfilamental structure must be (temporarily) destroyed before the formation and/or separation of cytoplasts and karyoplasts can take place. Similarly, optimal PMN cytoplast formation only takes place at temperatures above the transition temperature of the lipids in the PMN plasma membrane (i.e. 25° C.).

The PMN cytoplasts retain the immunological surface properties of the original PMN. This was shown by the following experiment.

PMN ($10^6$) or PMN cytoplasts ($3 \times 10^6$) were fixed with 0.5% (wt/vol) paraformaldehyde for 5 min. at room temperature and washed twice with phosphate-buffered saline (PBS). The cells were then incubated for 30 minutes at room temperature with 1:1000 dilutions of the monoclonal mouse IgG1 antibody B13-3 (30 mg of protein/ml; directed against a PMN plasma membrane antigen with a molecular weight of 87,000) or, as a control experiment, with the monoclonal mouse IgG1 antibody C17 (20 mg of protein/ml; directed against the thrombocyte plasma membrane antigen GP IIIa). After two washings with PBS, the cells were stained with a 1:80 dilution of a 11.8 mg protein/ml FITC-labeled goat-anti-mouse IgG (30 minutes, room temperature), washed twice with PBS and suspended in 70% (vol/vol) glycerol in PBS. Two hundred cells were scored as positive or negative by fluorescence microscopy.

The results showed that 99% of the original PMN and 96% of the PMN cytoplasts reacted with the antibody B13-3. In contrast, only 9% of the original PMN and the PMN cytoplasts reacted with the antibody C17. Thus, the PMN surface antigen that bound B13-3 was also present on the PMN cytoplasts, and both PMN and PMN cytoplasts lacked a surface structure that reacted with C17.

For quantitative measurement of B13-3 binding, this antibody was labeled with $^{125}$Iodide by the iodogen method. In brief, 100 μg of iodogen in 100 μl of dimethyl chloride was put into a 10 ml bottle, and the solvent was evaporated with dry nitrogen gas. Next, 100 μg of B13-3 in 200 μl of PBS+1 mCi Na$^{125}$I was added and incubated for 1 min at room temperature. The supernate was then dialyzed three times against 500 ml of PBS+0.01% (wt/vol) KI. Ten million PMN or $30 \times 10^6$ PMN cytoplasts were incubated for 45 min at room temperature with 0.8 ng of the $^{125}$I-labeled B13-3 together with 1.5 μg of unlabeled B13-3, in a volume made 300 μl with incubation medium. Thereafer, the PMN and the PMN cytoplasts were washed five times 10 ml of PBS plus 0.5% (wt/vol) human albumin. The radioactivity was counted in a gamma-radiation counter.

The results showed that PMN cytoplasts bound 36% of the amount of B13-3 bound by intact PMN. From other measurements of the surface area (alkaline phosphatase, relative volume assay) it had been calculated that the PMN cytoplasts have a surface area of 33% and 29%, respectively, of intact PMN. Thus, this indicates that the number of antigens that bind B13-3 per unit of surface area is equal in PMN cytoplasts and in intact PMN.

Alternatively, the PMN were incubated for 30 minutes at room temperature with a 1:5 dilution of F(ab') fragments of a rabbit-IgG antiserum against C3b receptor from human erythrocytes (0.6 mg protein/ml). F(ab') fragments of rabbit IgG against human IgG were used as a control. The PMN were washed twice with PBS, and part of the cells was then suspended in 12.5% (wt/vol) Ficoll and subjected to the cytoplast preparation. Next, the PMN and the PMN cytoplasts were fixed with 1% (wt/vol) paraformaldehyde and washed twice with PBS. Both preparations were then incubated for 30 minutes at room temperature with a 1:100 dilution of FITC-labeled F(ab') fragments of swine IgG against rabbit IgG (6 mg protein/ml), washed twice with PBS, suspended in 70% (vol/vol) glycerol in PBS and examined by fluorescence microscopy.

The results showed that 93% of the original PMN bound the antibody against the C3b receptor. When PMN cytoplasts were prepared from PMN with this antibody on their surface, 90% of the resulting PMN cytoplasts were found to carry this antibody. The control experiment with an irrelevant antibody was totally negative with both PMN and PMN cytoplasts. This indicates that surface antigens, even when complexed with an antibody, are carried from PMN to PMN cytoplasts during the preparation of the PMN cytoplasts.

The recovery of the enucleated PMN from the centrifugation tube is effected e.g. by means of a pipette, such as a Pasteur pipette. The fraction containing the enucleated PMN should be washed free from cytochalasin. This can be done e.g. by adding PBS optionally containing a protein, such as human albumin, BSA or fetal calf serum, centrifuging, and removing the supernatant. This washing procedure may be repeated, if necessary.

The enucleated cells (cytoplasts) may be stored in frozen condition, usually as a suspension in a medium having essentially the same osmolality as the cells. A cryoprotectant may be added, but this is not absolutely necessary, as the cytoplasts have been found to be remarkably insensitive to freezing. Suitable suspending media include phosphate buffered saline, Sarle's medium, Dulbucco's medium and Hank's balanced salt solution. If desired, glycerol, glycerol plus glucose, or dimethyl sulfoxide may be added to any of these media. Further, the media may contain a protecting protein, such as albumin (human or bovine), inactivated human serum, inactivated bovine serum, or, preferably, fetal calf serum.

A preferred medium for freezing and storage of the enucleated cells according to the invention is phosphate buffered saline containing 10% (vol/vol) fetal calf serum and 10% (vol/vol) dimethyl sulfoxide.

The cells are suspended in the selected medium, the suspensions brought into vials, such as ampoules, and after sealing, the vials are placed in a freezer, e.g. at $-70°$ C. for at least one hour.

Due to the retained immunological properties and the possibility of storage in frozen condition the granulocyte cytoplasts of the invention are excellently suitable for use in methods for assaying antibodies against granulocytes in aqueous samples, such as body fluids e.g. in blood plasma, blood serum, whole blood, blood cell eluates or IgC concentrates.

Therefore, the invention also relates to a process for assaying antibodies against granulocytes in a sample, which comprises incubating the sample with enucleated granulocytes, and detecting the formation and/or assaying the amount of any antigen-antibody reaction product formed.

The detection of any antigen-antibody reaction product formed may be effected by methods known per se.

When the antibody titer in the sample is sufficiently high the formation of a reaction product may be detected by observation of cell agglutination by means of a microscope. More sensitive methods are necessary when the antibody titer of the sample is too low for detection of cell agglutination, or when non-agglutinating antibodies are involved. Other, more sensitive methods include: the use of complement binding reactions, the use of labeled antibodies, and the use of a subsequent reaction with cytotoxic effector cells. When complement binding reactions are used, the antibody bound by the enucleated granulocytes is detected by a second reaction with complement components and measurement of the resulting cell lysis. The antibody bound by the enucleated cells also may be detected by a second reaction with cytotoxic effector cells and measurement of the resulting cell lysis. Detection by using labeled antibodies is preferred. This involves incubation of the antibody-enucleated granulocyte reaction product with a second, labeled antibody directed against the antigranulocyte antibody. The label may be e.g. fluorescent, enzymatic, or radioactive. These methods are known as immunofluorescence assays, enzyme immunoassays, and radio immuno-assays, respectively. The use of fluorescent antibodies is preferred, because immunofluorescence assays are easy to perform and are sensitive. A suitable fluorescent label may be introduced by reaction with fluorescein isothiocyanate (FITC). A suitable labeled antibody directed against the anti-granulocyte antibody bound onto the enucleated granulocytes is labeled antiglobulin serum. Preferably, fluorescein isothiocyanate labeled F(ab')$_2$ fragments of sheep IgG against human globulin are used.

Finally, the invention relates to a kit for carrying out the process for assaying antibodies against granulocytes in a sample. This kit comprises essentially containers with granulocyte cytoplasts, particularly PMN cytoplasts, typed for granulocyte-specific antigens, in a suspending medium, in frozen condition.

The suspending medium may be any of the known cell-suspending media used for storage of cells in frozen condition. Examples of suitable media are mentioned above.

The cytoplasts are preferably suspended in a medium consisting of phosphate buffered saline (PBS), pH 7.4 containing 10% (vol/vol) of fetal calf serum (FCT) and 10% (vol/vol) of dimethyl sulfoxie (DMSO).

Normally, the containers for the cytoplast suspension are ampoules of e.g. 2.5 ml. Each ampoule may contain e.g. $8 \times 10^6$ PMN cytoplasts in 2 ml of PBS-10% FCT-10% DMSO.

At present, five different antigens are known to be specific for granulocytes. Thus, at present, the kit has to contain PMN cytoplasts from five donors, each with a different specificity for these antigens. Naturally, the kit may contain more than one series of five different antigens, e.g. 20 ampoules with PMN cytoplasts from each of the donors having a different antigen specificity. Accordingly, such a kit contains 100 ampoules.

As the cytoplast suspensions should be shipped and stored in frozen condition the kits according to the invention are provided with means capable of maintaining the cytoplast suspensions in frozen condition, preferably at a temperature of −20° C. or lower, e.g. with an insulated dry ice cabinet.

All other reagents and instruments necessary for carrying out the assay are readily available in well-equipped laboratories, but the kit additionally may comprise containers with antiglobulin serum, preferably fluorescein isothiocyanate (FITC) labeled F(ab')$_2$ fragments of sheep IgG against human globulin.

Additionally, the kits according to the invention may comprise containers with:

(a) phosphate buffered saline pH 7.4,
(b) bovine serum albumin (60 gram/liter),
(c) human AB serum,
(d) aqueous glycerol solution, 21% (wt/vol),
(e) aqueous paraformaldehyde solution, 1% (wt/vol).

If necessary, the kits according to the invention may also comprise at least one microtiter plate and at least one microsyringe.

Moreover, the kits according to the invention may comprise operating instructions for carrying out the test.

The invention is illustrated by the following examples which are given for illustration purposes only and are not intended to limit the scope of the claims.

EXAMPLE 1

PMN were suspended in 12.5% (wt/vol) Ficoll solution (specific gravity $d^{20}$, 1.0477 gram/cm$^3$) with 20 μM cytochalasin B (Sigma Chemical Co., St. Louis, Mo., USA). This cell suspension (about $10^8$ PMN per ml) was preincubated for 5 min at 37° C. The suspension (4.5 ml) was then layered on a pre-warmed (2 h at 37° C.) discontinuous density gradient [4.5 ml of 16% (wt/vol) Ficoll ($d^{20}$, 1.0578) on top of 4.5 ml of 25% (wt/vol) Ficoll ($d^{20}$, 1.0855)]. Cytochalasin B (20 μM) was present throughout the gradient. Polycarbonate centrifuge tubes (2.5×8.9 cm; Beckman Instruments, Palo Alto, Calif., USA, nr. 336091) were used. The gradients were centrifuged for 30 min at 81,000 x g (middle of the tubes) and 33° C. in an ultracentrifuge (TGA 50, Kontron, Zürich, Switzerland), of which the SW-27 swing-out rotor (Beckman Instruments) had been pre-warmed for 4 h at 37° C.

After centrifugation, a band of enucleated PMN (band 1) was present at the interface of the 12.5 and 16% Ficoll solution. A second band was found at the interface of the 16 and 25% Ficoll solution; this band 2 contained a few intact PMN and some cell debris. The nuclei were pelleted at the bottom of the tubes (band 3).

The PMN cytoplasts were collected with a Pasteur pipette and washed five times with PBS containing 0.5% (wt/vol) human albumin, to remove the cytochalasin B (centrifugation: 10 min., 600 x g, room temperature). After the last centrifugation, the PMN cytoplasts were suspended in ice-cold PBS with 10% (vol/vol) fetal calf serum and slowly mixed with an equal volume of ice-cold PBS with 10% (vol/vol) fetal calf serum and 20% (vol/vol) dimethyl sulfoxide. Portions of 2 ml of this suspension, containing $8 \times 10^6$ PMN cytoplasts, were transferred to 2.5 ml glass ampoules, which were then sealed in a flame. The ampoules were placed in a polystyrene insulating box with 10 mm thick walls. The box was then placed in a freezer at −70° C.

Before freezing, the yield of PMN cytoplasts was found to be equal to the number of PMN applied to the Ficoll gradient. This indicates that each PMN gives rise to one PMN cytoplast. After thawing and washing (procedure: see Example 2), the yield of PMN cytoplasts was found to be 75% of the number of PMN cytoplasts that was subjected to the freezing procedure.

EXAMPLE 2

Leukocyte agglutination technique for the detection of antibodies against granulocytes in the serum of patients.

The test was carried out in accordance with the following instructions:

Materials

1. PMN cytoplasts from typed donors for all known granulocyte antigens.
2. Microsyringe of 50 μl.
3. Pooled serum from fresh blood of 10 male donors with blood group AB who have never been transfused (AB serum).
4. Tissue culture plates with flat-bottom wells.
5. Phosphate-buffered saline (PBS): 140 mM NaCl, 9.2 mM $Na_2HPO_4$, 1.3 mM $NaH_2PO_4$ (pH 7.4).
6. Bovine serum albumin (BSA): 6 gram/100 ml.
7. Prepare PBS-10% BSA: 9 parts of PBS with 1 part of BSA.
8. Prepare PBS-2.5% BSA: 39 parts of PBS with 1 part of BSA.

Technique

1. Prepare serum from 5 ml of blood of the patients to be tested.
2. Thaw one ampoule of PMN cytoplasts from each antigen type. Thaw at 37° C. (shaking) until the ice has almost completely melted, then put the ampoules in ice. Open ampoules, bring contents in 50-ml tubes (on ice) and slowly dilute 10-fold with PBS+10% BSA. Centrifuge at 1700 rpm for 8 min. at room temperature in a table centrifuge. Remove supernate, resuspend the pellets in 5 ml PBS+2.5% BSA and centrifuge again (same as above). Repeat this washing procedure. Resuspend the cytoplasts in 0.3 ml of PBS+2.5% BSA (final concentration: about $30 \times 10^6$ cytoplasts per ml). Keep on ice, mix immediately before use. Do not use more than a few hours after thawing.
3. The rest of the procedure is to be carried out in duplicate, for precision.
4. Put 5 μl of patient serum with a 50-μl microsyringe into the wells of the first horizontal row of a tissue culture plate.
5. Put 5 μl of a 1:4 dilution in PBS of patient serum in the wells of the second horizontal row.
6. Put 5 μl of normal AB serum in the wells of the third horizontal row (negative control).
7. Add 3 μl of cytoplast suspension of antigen type 1 to each of the three wells in the first vertical row, 3 μl of cytoplast suspension of antigen type 2 to each of the three wells in the second vertical row, etc., with a 50 μl microsyringe.
8. Cover the microtiter plate with a coverslip and incubate for 60 minutes at room temperature on a rotator (80 cycles/min.).
9. Read the agglutination reaction with an inverted light microscope (magnification 200×).

The results indicate that the PMN cytoplasts, either fresh or cryopreserved, show exactly the same specificity toward anti-sera with known antibodies as do the original PMN. This is true both for known positive and for known negative anti-sera. Also, when these sera were diluted, the PMN cytoplasts showed a positive agglutination test with the same dilutions as did the original PMN.

This technique demonstrates granulocyte-specific antibodies and agglutinating HLA antibodies.

EXAMPLE 3

Leukocyte fluorescence technique for the detection of antibodies against granulocytes in the serum of patients. This test was carried out in accordance with the following instructions:

Materials 1 to 8 same as in Example 2.
9. Paraformaldehyde solution 10 gram/liter.
10. Antiglobulin serum: FITC-labeled $F(ab')_2$ fragments of sheep IgG against human globulin. If needed, this antiglobulin serum can be diluted with PBS.
11. Glycerol 850 g/l; dilute 1:4 with PBS. Final concentration: 21% (wt/vol) glycerol.

Technique

1. Prepare serum from 5 ml of the blood of the patient to be tested.
2. Thaw and wash cytoplasts as described in Example 2. Keep on ice, mix immediately before use. Do not use more than a few hours after thawing.
3. Put into each tube of a horizontal row of 45×7 mm tests tubes two drops of the serum to be investigated. In a second row, put two drops of AB serum into each tube (negative control). In a third row, put into each tube a serum known to contain antibodies against granulocytes (positive control).
4. Add two drops of cytoplast suspension ($30 \times 10^6$/ml in PBS-2.5% BSA) to each tube so that each of the three tubes in a vertical row receive cytoplast suspension of a particular antigen type. Mix the tubes and incubate for 30 min. at 37° C.
5. Centrifuge the tubes (8 min, room temperature, 1700 rpm in table centrifuge). Remove supernate, suspend cells in 1 ml of PBS-2.5% BSA. Repeat this procedure twice.
6. Resuspend the cells in two drops of antiglobulin serum, and incubate the tubes for 30 min. at 37° C. in the dark. If necessary, dilutions of the antiglobulin serum in PBS can be tested.
7. Repeat step 5 (two washings).
8. Resuspend the cells in one drop of 21% glycerol, put the cells on a microscope slide and cover with a coverslip.
9. Read the fluorescence under a fluorescence microscope (water objective, 54×magnification). Reading can be postponed till the next day; the preparation must then be kept at 4° C. in the dark in the meantime.

The results indicate that the PMN cytoplasts, either fresh or cryopreserved, show exactly the same specificity toward anti-sera with known antibodies as do the original PMN. This is true both for known positive and for known negative anti-sera. Also, when these sera were diluted, the PMN cytoplasts showed a positive fluorescence test with the same dilutions as did the original PMN. With this technique the following antibodies can be demonstrated:
a. Non-agglutinating, non-complement binding, granulocyte-specific antibodies.
b. Most of the agglutinating and cytotoxic antibodies against granulocytes.
c. Antibodies against HLA determinants.

EXAMPLE 4

A test kit for detection and/or assay of antibodies against granulocytes contains 5 ampoules (2.5 ml) containing PMN cytoplasts ($8 \times 10^6$ cells in 2 ml of PBS-10% (vol/vol) FCT-10% (vol/vol) DMSO) (see Example 1). Each individual ampoule contains PMN cytoplasts from one donor typed for granulocyte-specific antigens. Thus, the five PMN cytoplast suspensions have different antigen specificities. The ampoules are stored in an insulated dry ice cabinet ($-20°$ C.).

EXAMPLE 5

The test kit of this example is the same as that of Example 4, with the difference that it contains 20 ampoules of each of the 5 antigen types, thus making 100 ampoules.

EXAMPLE 6

The test kit of this example is the same as that of Example 4 or 5, with the difference that it contains additionally a container with antiglobulin serum (FITC-labeled F(ab')$_2$ fragments of sheep IgG against human globulin).

EXAMPLE 7

The test kit of this example is the same as that of Example 4, 5 or 6, with the difference that it contains additionally containers with a. PBS (phosphate buffered saline; 140 mM NaCl, 9.2 mM Na$_2$HPO$_4$, 1.3 mM NaH$_2$PO$_4$; pH 7.4)
b. BSA (bovine serum albumin) 60 gram/liter
c. Human AB serum (pool of 10 AB donors)
d. Glycerol, 21% (wt/vol)
e. Paraformaldehyde, 1% (wt/vol) and optionally:
f. Microtiter plates with flat-bottom wells (e.g. Greiner, nr. 698180).
g. Microsyringe 50 μl (e.g. Hamilton).

If desired, the test kits according to any of the Examples 4 to 7 may contain operating instructions for carrying out the test, e.g. in accordance with Example 2 or 3.

We claim:

1. A process for assaying antibodies against granulocytes in a sample, which comprises incubating the sample with enucleated granulocytes, and assaying the incubated sample to detect the formation of the product formed by the reaction of enucleated granulocytes and antibodies against granulocytes.

2. The process of claim 1, which further comprises assaying the incubated sample to assay the amount of reaction product formed.

3. The process of claim 1 or 2, which comprises incubating a blood sample to be assayed with enucleated polymorphonuclear leukocytes, washing said incubated sample, incubating the washed sample with fluorescein isothiocyanate labeled antiglobulin serum, washing said labeled sample and reading the fluorescence of the reaction product formed.

4. The process of claim 1 or 2 in which the product formed by the reaction of enucleated granulocytes and antibodies against granulocytes is assayed by a means selected from the group consisting of observation of cell agglutination, complement binding reactions, labeled antibodies and subsequent reaction with cytotoxic effector cells.

5. The process of claim 4, in which the means are an immunofluorescence assay, an enzyme-immunoassay and a radio immunoassay.

6. A process of claim 3, in which the fluorescein isothiocyanate labeled antiglobulin serum is fluorescein isothiocyanate labeled F(ab')$_2$ fragments of sheep IgG against human globulin.

7. A kit having component parts capable of being combined for assaying antibodies against granulocytes, the kit comprising enucleated granulocytes typed for granulocyte-specific antigens, in a suspended medium, in a frozen condition.

8. The kit of claim 7 additionally comprising one or more labeled antiglobulin sera.

9. The kit of claim 8, in which the antiglobulin sera is fluorescein isothiocyanate labeled F(ab')$_2$ fragments of sheep IgG against human globulin.

10. The kit of claim 7, additionally comprising
 (a) phosphate buffered saline pH 7.4
 (b) bovine serum albumin (60 g/l)
 (c) human AB serum
 (d) aqueous glycerol solution 21% (wt/vol) and
 (e) aqueous paraformaldehyde solution 1% (wt/vol).

11. The kit of claim 10, in which the enucleated granulocytes are enucleated polymorphonuclear leukocytes.

12. The kit of claim 11 in which the suspending medium for the enucleated polymorphonuclear leukocytes is phosphate buffered saline, pH 7.4, containing 10% (vol/vol) fetal calf serum and 10% (vol/vol) dimethyl sulfoxide.

* * * * *

UNITED STATES PATENT AND TRADEMARK OFFICE
CERTIFICATE OF CORRECTION

PATENT NO. : 4,623,620

DATED : November 18, 1986

INVENTOR(S) : Dirk Roos et al.

It is certified that error appears in the above-identified patent and that said Letters Patent is hereby corrected as shown below:

Col. 3, line 51, "Thereafer" should read --Thereafter--; and

Col. 10, line 43, "claim 10" should read --claim 7--.

Signed and Sealed this

Twenty-eighth Day of April, 1987

Attest:

DONALD J. QUIGG

Attesting Officer

Commissioner of Patents and Trademarks